US 6,403,100 B1

(12) United States Patent
Barry, III et al.

(10) Patent No.: US 6,403,100 B1
(45) Date of Patent: Jun. 11, 2002

(54) METHOD OF ATTENUATING PATHOGENIC MYCOBACTERIA AND STRAINS OF MYCOBACTERIA SO ATTENUATED

(75) Inventors: Clifton E. Barry, III, Bethesda, MD (US); Ying Yuan, Bellevue, WA (US); Deborah D. Crane, Hamilton, MT (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/462,556

(22) PCT Filed: Jul. 9, 1998

(86) PCT No.: PCT/US98/14227

§ 371 (c)(1),
(2), (4) Date: Jun. 27, 2000

(87) PCT Pub. No.: WO99/02670

PCT Pub. Date: Jan. 21, 1999

Related U.S. Application Data

(60) Provisional application No. 60/052,199, filed on Jul. 10, 1997.

(51) Int. Cl.[7] ..................... A61K 39/04; A61K 49/00; C12N 15/00; C12N 15/74; C12N 1/00
(52) U.S. Cl. ............... 424/248.1; 424/9.1; 424/9.2; 424/93.1; 424/93.2; 424/184.1; 424/234.1; 435/68.1; 435/86.3; 435/86.4; 435/86.5; 435/866; 435/440; 435/471
(58) Field of Search .................. 424/88, 9.2, 93.1, 424/9.1, 184.1, 234.1, 248.1, 93.2; 435/68.1, 863–866, 440, 471

(56) References Cited

U.S. PATENT DOCUMENTS 4,724,144 A * 2/1988 Rook et al. .................... 424/88

FOREIGN PATENT DOCUMENTS

WO        WO92/22326    * 12/1992   .......... A61K/39/04

OTHER PUBLICATIONS

Wiegeshaus et al, "Evaluation of the Protective Potency of New Tuberculosis Vaccines", Reviews of Infectious Diseases, vol. 11, supplement 2, pp. S484–S490, Mar.–Apr. 1989.*
Lee, B–Y, et al, "Characterization of the Major Membrane protein of virulent *Mycobacterium tuberculosis*", Infection and Immunity, vol. 60, No. 5, pp. 2066–2074, May 1992.*
Verbon, A., et al, "The 14,000 molecular weight antigen of *Mycobacterium tuberculosis* is related to the alpha–crystallin family of low–molecular–weight heat shock proteins", Journal of Bacteriology, vol. 174, No. 4, pp. 1352–1359, Feb. 1992.*
Yuan, Y., et al, "Stationary phase–associated protein expression in *Mycobacterium tuberculosis*: function of the mycobacterial alpha–crystallin homolog", Journal of Bacteriology, vol. 178, No. 15, pp. 4484–4492, Aug. 1996.*
Fuerst, T.R., et al, "Development of BCG as a live recombinant vector system: Potential use as an HIV vaccine", Biotechnology Therapeutics, vol. 2, No. 1–2, pp. 159–178, 1990.*
jacobs, Jr., W.R., et al, "Introduction of foreign DNA into mycobacteria using a shuttle phasmid", Nature, vol. 327, pp. 532–535, Jul. 1987.*
Baldwin, S.L., et al, "Evaluation of new vaccines in the mouse and guinea pig model of tuberculosis", Infection and Immunity, vol. 66, No. 6, pp. 2951–2959, Jun. 1998.*
Orme, I.M., et al, "Tuberculosis vaccine development: recent progress", Trends in Microbiology, vol. 9, No. 3, pp. 115–118, Mar. 2001.*
Orme, I.M., "New vaccines against tuberculosis", Infectious Disease Clinics of North America, vol. 13, No. 1, pp. 169–185, Mar. 1999.*

* cited by examiner

*Primary Examiner*—Rodney P Swartz
(74) *Attorney, Agent, or Firm*—Townsend and Townsend and Crew, LLP

(57) ABSTRACT

This invention provides for novel attenuated strains of *Mycobacterium tuberculosis* and *M. bovis*. Attenuation is achieved by eliminating or by downregulating the expression of the α-crystallin heat shock protein gene ("acr gene"). The invention provides for vaccines and methods of vaccinating mammals for protection against Mycobacterium sp. that cause tuberculosis.

11 Claims, No Drawings

METHOD OF ATTENUATING PATHOGENIC MYCOBACTERIA AND STRAINS OF MYCOBACTERIA SO ATTENUATED

CROSS-REFERENCE TO RELATED APPLICATIONS

This application claims priority from the filing date of U.S. Provisional Application No. 60/052,199, filed Jul. 10, 1997.

BACKGROUND OF THE INVENTION

1. Field of the Invention

This invention provides novel attenuated strains of pathogenic mycobacteria and, in particular, of *Mycobacterium tuberculosis* and *M. bovis*. Attenuation is achieved by down-regulating or eliminating the expression of the α-crystallin heat shock protein gene ("acr gene"). The invention also provides vaccines and methods of vaccinating mammals for protection against mycobacterial diseases including, in particular, tuberculosis.

2. Relevant Art

Pathogenic mycobacteria are the causative agents of a number of human and animal diseases. For example, tuberculosis is a health problem of considerable importance in the human population. Recent estimates are that as much as one-third of the population of the world is infected with *M. tuberculosis*, that there are 30 million active cases, that there are some 10 million new cases annually, and that tuberculosis causes some 6 percent of all deaths worldwide. See, e.g., Daniel, T., Tuberculosis in Harrison et al., eds., *Principles of Internal Medicine*, McGraw-Hill, Inc., New York, N.Y. (13th ed., 1994) (hereafter "Harrison's (1994)"; the entirety of Harrison's is hereby incorporated by reference). At present, the only vaccine is an attenuated strain of *M. bovis* designated bacillus Calmette-Guerin ("BCG"). While this vaccine is considered safe, its efficacy is still uncertain. Ibid.

BCG is created by multiple passages of the *M. bovis* organism. These multiple passages are considered necessary to attenuate the pathogenicity of the organism but, as the organism adapts to laboratory passaging, it undergoes undefined and unknown changes from that of the wild type. These changes, in turn, diminish the relevance of the immune response generated by use of BCG to subsequent challenge by wild type, pathogenic bacteria, and are probably due at least in part to the continuing uncertainty over its efficacy. Moreover, since *M. bovis* infects cows, rather than humans, a portion of the immune response it raises is not directed against antigens relevant to human disease.

What is therefore needed is a method of producing attenuated mycobacteria without the multitude of passages currently necessary to produce BCG, so that the immune response generated is more relevant to the challenge posed by wild type, pathogenic bacteria. What is also needed, in particular, is a vaccine for tuberculosis based on mycobacteria less removed from the wild type than are those used to create BCG. What is even more needed is a vaccine which is based on *M. tuberculosis*, and which can therefore be expected to raise an immune response more directly relevant to the antigens presented by wild type *M. tuberculosis*. It would further be desirable to have a vaccine of organisms capable of replicating for a short time in a vaccinated host, to permit the organism to present proteins and other antigens which may only be presented live, metabolizing organisms, but also capable of being completely contained by the host. The present invention provides these and other advantages.

SUMMARY OF THE INVENTION

This invention provides a vaccine for protection against tuberculosis. The vaccine comprises pharmaceutically acceptable excipients and Mycobacterium sp. attenuated by having the expression level of the α-crystallin heat shock protein gene reduced by at least 75% of the wild type expression level, said Mycobacterium sp. being present in a concentration effective to provide immunoprotection to a host mammal. In preferred embodiments, expression of the α-crystallin heat shock protein gene is eliminated. In more preferred forms, the gene for the protein is "knocked out."

In one embodiment, the vaccines have the Mycobacterium sp. in an isotonic salt solution. Preferred dosages are between 1 and around 1,000,000 cells per dose. More preferred dosages are between around 100 and around 100,000 cells per dose. Somewhat more preferred are between around 100 and around 50,000 cells per dose. Even more preferred are between around 100 and around 25,000 cells per dose. Most preferred are between around 100 and around 1,000 cells per dose.

This invention also provides for a method of vaccinating a mammal susceptible to an infection of Mycobacterium sp. The method comprises the administration of an amount of Mycobacterium sp. attenuated by having the expression level of α-crystallin heat shock protein gene reduced by at least 75% of the wild type expression level, said administration of Mycobacterium sp. in an amount effective to provide immunoprotection to a host mammal. Preferred routes of administration are via the nasal passages or via parenteral injection. The preferred dose is between 100 and 100,000 cells, depending, inter alia, on the route of administration.

In addition to vaccines and methods of vaccinating, this invention provides for novel strains of Mycobacterium sp. wherein the expression level of the α-crystallin heat shock protein gene is reduced by at least 75% compared to the wild type expression level. In one embodiment, the strains are housed in a sealed vial where the vial is packaged with instructional material stating a method of injecting the strain into a human to provide the human with immunoprotection from tuberculosis.

In one embodiment of the vaccine, methods, and strains described above, the Mycobacterium species is selected from the group consisting of *M. tuberculosis* and *M. bovis*.

Additionally, the invention provides a method of manufacturing attenuated mycobacteria by reducing the expression of the α-crystallin heat shock protein gene by at least 75% compared to the wild type expression level. In one embodiment, the reduction is by deletion of the gene encoding the protein. In preferred embodiments, the mycobacteria manufactured by this method are *M. tuberculosis* or *M. bovis*.

Further, the invention provides a method for attenuating virulence of a Mycobacterium sp., wherein the method comprises reducing the expression of the α-crystallin heat shock protein gene by at least 75% compared to the wild type expression level. In one embodiment, the reduction is by deletion of the gene encoding the protein. In preferred embodiments, the mycobacteria whose virulence are attenuated by this method are *M. tuberculosis* or *M. bovis*.

DEFINITIONS

"Attenuated" refers to a state of reduced pathogenicity of an organism that in its wild state is pathogenic. It is usually measured by an inhibition, partial or complete, of the ability of a pathogenic organism to colonize, infect, grow, reproduce, or survive in a host. When attenuation is due to a defined genetic change, that change may be a gene deletion, replacement, or alteration, transcriptional inhibition, or translational inhibition.

"Imnmunoprotection" refers to the ability of the immune system of a mammal such as a human to reduce infection of a pathogen such as *M. tuberculosis* or *M. bovis* when challenged with what would otherwise be an infectious dose.

"Isotonic salt solutions" are salt solutions that are osmotically balanced against the cells in which they are contacted. They are preferably at physiologic pHs of between 6.5 and 7.5.

"Instructional material" refer to written, audio or visual means to convey the proper use of material or pharmaceuticals, vaccines or reagents.

"Pharmaceutically acceptable" means a material that is not biologically or otherwise undesirable, i.e., the material can be administered to an individual along with the acr attenuated mycobacteria without causing any undesirable biological effects or interacting in a deleterious manner with any of the other components of the pharmaceutical composition.

The phrase "expression level of α-crystallin heat shock protein gene reduced by at least 75% of the wild type expression level" refers to a reduction of at least 75% in the relative level of expression of α-crystallin heat shock protein between a wild type pathogenic strain and a strain deliberately altered to reduce natural levels of the protein, measured by any scientifically valid technique. Typically, measurements of relative level involve labeling antibodies specific to the α-crystallin heat shock protein or labeling probes which specifically hybridize to nucleic acids encoding the protein in genomic DNA or mRNA. Methods of altering the relative level of expression are not limited to gene "knock out" and include methods of interference with mRNA transcription or with translation, including interference with translation by means of antisense or ribozyme technology.

As used herein, "strain" has two meanings. With respect to a wild type microorganism, "strain" refers to a substantially pure culture of a mycobacterial species, and is commonly applied to a culture of mycobacteria isolated from a patient or cluster of patients manifesting disease. With respect to a microorganism whose expression of the α-crystallin heat shock protein has been altered from that of the corresponding wild type, such as recombinantly altered organisms, "strain" refers to a substantially pure culture of a mycobacterial species wherein the microorganisms are at least 70% homogeneous in their expression of the α-crystallin heat shock protein. More preferably, at least 80% of the microorganisms are homogeneous in their expression of this protein. Even more preferably, the homogeneity is around 90% or above. Most preferably, the microorganisms are homogeneous in not expressing detectable levels of this protein.

"Vial" refers to any container that is sealed from the atmosphere and able to hold within it a liquid or freeze dried material without measurable losses.

DETAILED DESCRIPTION

This invention arises from the surprising discovery that Mycobacterium sp. such as *M. tuberculosis* and *M. bovis* can be attenuated by downregulating the expression of the α-crystallin heat shock protein gene. More surprisingly this novel attenuated strain has the ability to confer immunoprotection to animals susceptible to infections from Mycobacterium sp.

1. Obtaining Forms of Mycobacterium sp. Attenuated by Downregulating Or Eliminating Expression of Acr To obtain attenuated forms of Mycobacterium sp., one starts with standard pathogenic strains of organisms such as *M. tuberculosis* or *M. bovis*. Strain H37Rv is typical of the pathogenic forms of *M. tuberculosis*. Qualified individuals can obtain this strain from the American Type Culture Collection, located at 10801 University Boulevard, Manassas, Va., USA. The accession number is 27294. Other strains are available from Colorado State University, Fort Collins under the NIAID "Tuberculosis Research Materials" contract (administered by Dr. Ann Ginsberg, Tuberculosis Program Officer, NIAID, Solar Building, Room 3A31, Bethesda Md. 20892.

To maximize immunoprotection from a vaccination, it is generally desirable to maximize exposure to antigens present in virulent strains of the wild-type organism. Therefore, while various species and strains of mycobacteria can be used, it is preferable to use *M. tuberculosis* or *M. bovis*. *M. tuberculosis* is the most preferred species where the attenuated form is intended to vaccinate humans against tuberculosis, since it is the form most relevant to the human disease. It is further preferable to use a strain which has been isolated relatively recently from clinical specimens (that is, a strain which has not undergone a large number of passages). Such a strain is CSU93, a recently isolated hypervirulent strain. CSU93 is available to qualified investigators from Dr. John Belisle of Colorado State University under the terms of the NIAID contract mentioned above. Strains of mycobacterium already attenuated in other aspects can also be used. *M. bovis* bacillus Calmette-Guerin ("BCG"), which is considered to have multiple, but unknown, alterations due to multiple passaging, can be used and, indeed, can be expected to require less passaging before being suitable for use because of the reduced pathogenicity imparted by the reduction or elimination of the α-crystallin heat shock protein. BCG would, however, be expected to produce a less robust immune response than a more recent isolate and is therefore less preferred.

The target gene, α-crystallin heat shock protein gene ("acr gene") is known and its sequence is a matter of public knowledge. The acr gene was first published in 1992 by two groups (Verbon et al., *J. Bacteriol.* 174: 1352–1359 (1992); Lee et al., *Infect. Immun.* 60: 2066–2074 (1992)). The 14,000-molecular weight antigen of *M. tuberculosis* is related to the α-crystallin family of low-molecular weight heat shock proteins. The amino acid and nucleic acid sequences are published in GenBank and have the following GenBank Accession Numbers; S79751 and M76712.

Mycobacterium sp. can be maintained under appropriate culture conditions (see, e.g., Yuan et al., *J. Bacteriol.* 178: 4484–4492 (1995)). While the organisms can be grown on any of a large number of media well known to those of skill in the art, a preferred medium is Middlebrook 7H9 (Remel Laboratories, Lenexai, Kans.), supplemented with albumin-dextrose complex ("ADC"), available from Difco (Detroit, Mich.).

There are a number of conventional methods for selectively downregulating the expression of a specific protein. These include gene removal, replacement, transposition, antisense technology, and ribozyme technology.

Gene deletion is a preferred method because the gene is fully disabled by removal. The acr gene is contained entirely within a 4 kb BamHI restriction fragment. One way to eliminate production of the protein is to replace the gene encoding this protein with an antibiotic resistance cassette such as hygromycin or kanamycin. These resistance cassettes have been previously described in George et al., *J. Biol. Chem.* 270: 27292–27298 (1995). The antibiotic marker can be used to replace a segment of the gene or the whole gene. In this case, the acr gene is contained entirely on a 1 kb EcoRV fragment that is internal to the 4 kb BamHI fragment described above. Restriction digestion of the BamHI fragment with EcoRV removes the 1 kb EcoRV fragment. The resulting ligation of a blunt-ended antibiotic resistance cassette in place of the 1 kb EcoRV fragment into the BamHI fragment produces a construct lacking the α-crystallin gene. Transformation of Mycobacterium sp. with either linear or supercoiled DNA will result in gene replacement in a small fraction of the resulting organisms. Those organisms can then be selected by testing for antibiotic resistance added by the replacement cassette and cultured to provide the quantities of attenuated organisms desired.

Antisense technology is another viable method for down-regulation of acr gene expression. Expression of the α-crystallin gene can be interrupted at the level of transcription by overproducing a small segment of RNA encoding a sequence contained on the sense strand of the normal α-crystallin gene. Overproduction of, for example, the first 30 nucleotides of the gene would result in an inhibition of transcription of the normal acr gene.

Gene knockout of the acr gene can also be achieved via transposition. Insertional mutagenesis of the acr gene could be achieved using a number of different random transposition systems. Such a system might be the recently described IS1096-derived transposon by McAdam et al., *Infection & Immunity* 63: 1004–1012 (1995). Such transposons would be marked with a suitable resistance gene, such as kanamycin, hygromycin, streptomycin or others, and random transposants would be selected for antibiotic resistance before screening for transposition within the acr gene.

Ribozyme technology is a ready means to selectively target specific mRNA for cleavage prior to its being expressed. A general review of this technology is found in Castanotto et al., *Crit. Rev. Eukaryotic Gene Expression* 2: 331–357 (1992), Castanotto et al., *Advances in Pharmacology* 25:289–317 (1994), and Haseloff & Gelach, *Nature* 334:585–591 (1988). In general there are two main types of available ribozymes, hammerhead and hairpin ribozymes. See, e.g., Rossie et al., Pharmac. Ther. 50:245–254 (1991) (hammerhead ribozymes) and Hampel et al., Nucl. Acids Res. 18:299–304 (1990); U.S. Pat. No. 5,254,678 (hairpin ribozymes). Either form can be modified in its substrate binding regions to selectively bind to and cleave mRNA encoding the acr gene. At least 30 ribozymes have been demonstrated to be effective in cells at disabling a variety of viral and endogenous substrates, as tabulated by Stull and Szoka (Pharma. Res. 12(4):465–483 (1995)). More specific information on creating optimized ribozymes for a select target, such as the α-crystallin heat shock protein, can be found in WO 96/01314, U.S. Pat. No. 5,496,698, and Campbell & Cech, *RNA* 1: 598–609 (1995). In brief, genes encoding ribozymes are transfected into the Mycobacterium sp. and are expressed at a level that directs the desired reduction of expression.

2. Determining Attenuation of the Acr Gene

Once a Mycobacterium sp., such as *M. tuberculosis* or *M. bovis*, has been modified to reduce the expression levels of acr gene, it is desirable to monitor and measure the level of reduction. Our studies have demonstrated the ability to completely eliminate the expression of the gene. The reduction, however, does not need to be 100% complete to render the attenuated strain useable as a vaccine. The reduction need only be sufficient to reduce pathogenicity to a level that eliminates clinical manifestation of disease, while still evoking a protective immune response.

There are several standard means to measure and quantify expression levels of the acr gene. These include Southern, Northern, and Western blotting techniques. An extensive guide to the hybridization of nucleic acids is found in Tijssen, *Laboratory Techniques in Biochemistry and Molecular Biology—Hybridization with Nucleic Acid Probes* part I, chapter 2 (1993). Other suitable references for detection of nucleic acids are Sambrook et al., *Molecular Cloning: A Laboratory Manual* (2d ed. 1989) and *Current Protocols in Molecular Biology*, (Ausubel et al., eds., 1987)

For a Southern blot analysis, one simply selects a region of the α-crystallin heat shock protein gene as a probe (about 500 bases or more in length) and analyzes the chromosomal DNA from a test sample of potentially attenuated Mycobacterium sp. The DNA is digested with any number of different restriction enzymes and then transferred to a filter such as nitrocellulose. The transferred DNA is then screened by hybridization with the above probe, which has been radiolabelled using standard, commercially prepared reagents. An attenuated strain would be characterized by a lack of, or reduced levels of, hybridization with the α-crystallin heat shock protein gene specific probe and/or a corresponding change in restriction pattern as detected by the probe and/or a corresponding change in the size of the restriction fragments as compared to wild type. In addition, a probe that corresponds to the inserted nucleic acid can be used as a positive marker for gene replacement.

Alternatively, one could use a Western blot analysis to determine reduced levels of α-crystallin heat shock protein. The α-crystallin heat shock protein is a major cell surface protein of *M. tuberculosis* and has been isolated and purified (see, e.g., Yuan et al., *J. Bacteriol.* 178: 4484–4492 (1996)) (hereafter, Yuan et al., 1996). Specific polyclonal and monoclonal antibodies are prepared using conventional techniques. The antibodies are then used to screened against cell lysates of attenuated Mycobacterium sp. which have been disrupted and separated using any of a variety of electrophoretic separation techniques. Antibodies to α-crystallin heat shock protein are available. The monoclonal designated F22-2 has been deposited with the Centers for Disease Control/World Health Organization Collection of Antibodies to mycobacteria.

One could also use Northern blot analysis to measure changes in transcription levels of acr gene. The total RNA is isolated from cells using standard techniques, typically by using strong disruptants. The RNA is separated according to size using any of a number of conventional electrophoresis techniques and transferred to a filter; the RNA is then probed with a labeled probe specific for the coding region of the acr gene. For example, one can obtain a suitable probe by using polymerase chain reaction ("PCR") technology to amplify a subsequence of the coding sequence of the GenBank-listed nucleotide sequence provided above. The following primer pair is suitable for this purpose: nucleotides 11–30 and 451–470. An attenuated strain would be characterized by a lack of, or reduced level of, hybridization with the probe, detection of a transcript with an altered size as compared to wild type, or both. In addition, a probe that corresponds to the inserted nucleic acid can be used as a positive marker for gene replacement.

Yet another alternative is to use amplification of the DNA or RNA, by PCR, ligase chain reaction ("LCR"), or the like. Standard techniques for performing such assays are known in the art (see, e.g., Eckert & Kunkel, PCR *Methods and Applications* 1: 17 (1991); Innis, M., et al., eds., *PCR Protocols* 1990 (Academic Press, San Diego Calif.);Wallace et al., *Ligase Chain Reaction,* in Pfiefer, G., ed., *Technologies for Detection of DNA Damage and Mutations* (Plenum Publishing Corp, New York, N.Y., 1996), pp. 307–322). When RNA is amplified it is first reverse transcribed into cDNA. The DNA (either cDNA or genomic DNA) is then amplified under controlled conditions using a suitable pair of primers to yield reproducible and quantifiable data for determining the original amount of α-crystallin heat shock protein gene specific transcript or gene present in a test sample. As described above, an attenuated strain would be characterized by amplification bands that have altered sizes or that are missing. In addition, the replacement nucleic acid can also be amplified as a positive confirmation that the acr gene has been replaced.

3. Formulation of Vaccines

Having downregulated the expression of α-crystallin heat shock protein in a Mycobacterium sp. strain and having evidence that the downregulation is sufficient to produce an attenuated strain of Mycobacterium sp., one then formulates the vaccine.

The attenuated strains can be raised in, for example, Middlebrook 7H9 liquid media supplemented with albumin-dextrose complex, 0.2% glycerol, and 0.05% Tween-80, as described in Yuan et al., (1996). Other media known in the art can, however, be used. Cultures are typically begun by inoculation from single colonies of organisms confirmed to be acr gene disruptants. If the organisms have had the acr gene replaced with a gene conferring resistance to an antibiotic, then the organisms will typically be grown on media supplemented with the antibiotic to which resistance-has been conferred, for example, 50 μg/ml hygromycin when the target gene has been replaced by a hygromycin resistance gene. The cultures are grown to an optical density (read at 650 nm) of 1.0, which corresponds to a cell density of about $1\times10^9$ colony forming units per ml of Mycobacterium sp.

For vaccine administration, the acr attenuated mycobacteria are typically combined with a pharmaceutically acceptable carrier appropriate for the intended mode of administration. Pharmaceutical compositions include a unit dose of the acr attenuated mycobacteria in combination with a pharmaceutically acceptable carrier and, in addition, can include other medicinal agents, pharmaceutical agents, carriers, adjuvants, diluents, and excipients. The proportion of acr attenuated mycobacteria and adjuvant can be varied over a broad range so long as both are present in effective concentrations as described below.

Examples of pharmaceutically acceptable carriers include solutions such as normal saline, Ringer's solution, PBS (phosphate-buffered saline), and generally mixtures of various salts including potassium and phosphate salts, with or without sugar additives such as glucose. Suitable carrier solutions also include, for example, water, dextrose, glycerol, or buffered vehicles. Nontoxic auxiliary substances, such as wetting agents, buffers, or emulsifiers may also be added to the composition. Adjuvants are generally commercially available from various sources.

4. Administration of the Vaccines

The pharmaceutical compositions of the invention can be administered by any suitable means, e.g., parenterally (subcutaneously, intramuscularly, or intraperitoneally), intravenously, nasally or orally. Preferably, the compositions are administered nasally, with aerosol administration being a preferred mode. Injectables can be prepared in conventional forms. An appropriate evaluation of the time and method for delivery of the vaccine is well within the skill of the clinician.

Vaccine compositions of the invention are administered to humans and other mammals susceptible to or otherwise at risk of infection to elicit an immune response against the mycobacteria and thus enhance the patient's own immune response capabilities. Such an amount is defined to be an immunogenically effective amount.

The exact amount of such pharmaceutical compositions required will vary from subject to subject, depending on the species, age, weight and general condition of the subject, the particular mycobacteria used, the mode of administering it, the nature of the formulation, and the like. The judgment of the prescribing physician is also an important consideration. Generally, dosage will approximate that which is typical for the administration of other live attenuated vaccines (see, e.g., Ravn et al., *J. Immunol.* 158: 1949–1955 (1997) (administration to humans); Chambers et al., *J. Immunol.* 158: 1742–1780 (1997) (administration to mice); Roia, F. *Immunizing Agents and Diagnostic Skin Antigens,* in Gennaro, A., ed., *Remington's Pharmaceutical Sciences,* Mack Publishing Company, Easton, Pa. (17th ed., 1985 and 18th ed., 1990) (the entirety of both of these editions of Remington's are hereby incorporated by reference).

Natural infections are believed to occur from exposure to as few as 1 to 10 organisms. Clearly, however, the chances of becoming infected go up the number of organisms increases, although there can be expected to be a point of diminishing returns. For purposes of vaccination, the number of acr attenuated mycobacteria for an aerosol administration can range from 1 to as many as about $10^6$ cells per dose. Preferably, the number of cells administered will range between about $10^2$ and about $10^4$ cells per dose, and more preferably are between about $10^2$ and about $10^3$ cells per dose. For parenteral administration, the number of cells can also range from about 1 to about $10^6$ cells per dose, with about $10^4$ cells per dose being preferred. For oral administration, the dose range is preferably about $10^4$ to about $10^7$ cells, with doses on the lower end of the range being preferred. A suitable dose size is about 0.1–5 ml, preferably about 0.1–1 ml. Accordingly, a typical dose for aerosol administration for example, would comprise 0.1 to 0.5 ml containing about $1\times10^3$ cells, or for subcutaneous administration, 0.1 to 0.5 ml containing about $1\times10^4$ cells.

The timing of administration of the vaccine and the number of doses required for immunization can be determined from standard live attenuated vaccine administration protocols. Typically, this vaccine composition will be administered in one dose (see, e.g., Product Information, *Physicians Desk Reference* (1996); *Remington's,* supra).

Lyophilization of the bacterial cells, and resuspension in a sterile solution prior to administration is will be a preferred embodiment of the invention in countries in which availability of refrigeration in the field or rural areas may be problematic, and is likely to be preferred in this country where ease of storage is desired. Frozen aliquots of vaccine, which can be thawed and injected without the need for resuspension, are likely to be preferred where these two factors are not major concerns since freezing results in better viability of the organisms than does lyophilization.

5. Confirming Immunization

Confirmation of immunization using the vaccine of the invention is typically performed by the tuberculin test. The standard antigen for the test is tuberculin purified protein derivative ("PPD"), also known as "old tuberculin." This antigen is a heterogenous and undefined substance prepared from mycobacteria culture filtrates. PPD is prepared according to standard procedures (see, e.g., Landi, *Applied Microbiol.* 11: 408 (1963)). More purified antigens are also available and may be used in place of PPD.

A standardized dose of PPD antigen is typically administered via an intracutaneous injection in the forearm in what is often called the tuberculin, or Mantoux, test (see Harrison's (1994) at 714–715; McMurray, D., in Baron, ed., *Medical Microbiology,* Churchill Livingstone, New York, N.Y. (3d ed., 1991) at 459). Multiple intracutaneous puncture or tine tests are also used.

The immune reaction to the antigen is read by measuring the transverse diameter of induration (the raised, hard area of inoculation with the antigen) at 48 to 72 hours. As a test of immunization (not diagnosis), an induration size of 5–10 mm is generally considered doubtful and an induration size of 10–15 mm is considered a successful immunization. Typically, the size of an induration on an immunized person will be greater than 15 mm. Because PPD reactivity seems to decrease with age, it may be useful to administer a repeat test on an older person with an intermediate dose of PPD 7 to 10 days after the first test. According to Harrison's (1994), a reaction to the second test should be considered significant. False negative tests are common, often resulting from technical errors such as subcutaneous injection, use of outdated PPD, or permitting PPD to remain in the syringe before use.

6. Alternative Uses for Attenuated Strains

Production of human vaccines against tuberculosis is an important part of this invention; however that is not the only use of the attenuated strains of the invention. Attenuated forms of *M. bovis* (which, as noted in the Background section, supra, infects cows), can also be used, for example, as a veterinary vaccine to protect cows and other animals against that organism. Other pathogenic mycobacteria expressing the acr protein and acr homologs, such as the members of the tuberculosis complex, can also be attenuated by the inventive method. Additionally, since vaccination of humans with BCG (an attenuated form of *M. bovis*) provides some protection against *M. leprae,* the causative agent of leprosy (see McMurray, D., *Mycobacteria and Nocardia,* in Baron, supra, at 452: "vaccination with *M. bovis* BCG has been effective in some endemic areas"), in addition to whatever protection it confers against tuberculosis, it is expected that vaccination with attenuated pathogenic mycobacteria such as *M. tuberculosis* and *M. bovis* will confer at least some protection against diseases caused by other pathogenic mycobacteria as well.

Nor are vaccines the only use of the attenuated strains of the invention. The physiology of slow-growing pathogenic species of mycobacteria is unique in many respects related to their preferred niche of growth within mammalian macrophages. Because of the risk of infection of laboratory workers, however, many laboratories engaged in mycobacterial research employ instead as models fast-growing species of mycobacteria, which are saprophytic and non-pathogenic. These species are extremely limited in their ability to predict drug efficacy against pathogenic forms, or the efficacy of potential vaccines or diagnostic products for pathogenic species. For example, high-throughput drug screening programs currently use a non-pathogenic mycobacterium, *M. aurum,* as a model organism to screen potential drug candidates. The attenuated forms of pathogenic mycobacteria provided by the invention are much closer models of the target organisms, and accordingly provide a significantly improved tool for screening for novel antimycobacterial agents.

In addition, subcellular fractions of pathogenic mycobacteria are common components of commercial products, such as the composition referred to as PPD, described above. This mixture of Mycobacterium sp. cellular debris is used on a global scale by health workers for detection of exposure to *M. tuberculosis* and *M. bovis.* Such fractions are also commonly used for commercial adjuvants, such as Freund's complete adjuvant and RibiImmunochem Research's (Hamilton, Mont.) MPL adjuvant. In addition, these attenuated strains can be used as diagnostics, including use as reagents for the development of monoclonal antibodies to recognize wild type mycobacteria in patient samples. Because of the reduced risk of infection of personnel, the attenuated forms of mycobacteria provided by the invention are a significant improvement over wild type strains for such purposes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Knocking Out the Acr Gene in *Mycobacterium tuberculosis*

A. Reagents and Culture Techniques

*Mycobacterium tuberculosis* strain H37Rv (ATCC 27294) and *Mycobacterium smegmatis* strain mc2155 (NIH AIDS Research and Reference Reagent Program) were grown and labeled as previously described in Yuan et al., (1996).

B. Genetic Constructs and Knockout Generation

The gene replacement vector was constructed by first removing the EcoRV restriction enzyme site from pBluescript II KS+ (Stratagene, LaJolla, Calif.) by digestion with HincII and EcoRV. Klenow-mediated fill-in and religation gave the modified pBluescript derivative which was then restricted with BamHI and ligated with the purified 4 kb BamHI fragment from pMV206H:$\alpha$-Crsyt. This construct was digested with EcoRV to remove the internal 1 kb fragment containing the $\alpha$-crystallin gene and the gel-purified larger fragment was blunt-end ligated with a hygromycin resistance cassette, which has been previously described (George et al., *J. Biol. Chem.* 270: 27292–27298 (1995)). After purification and verification, this construct was linearized with BamHI and used to transform H37Rv to hygromycin resistance as described in Yuan et al. *J. Biol. Chem.* 272: 10041–10049 (1997). Hygromycin-resistant single colonies were picked and grown to saturation in 2 ml cultures. Bacteria were harvested by centrifugation and lysed by bead-beating for 2 minutes. Lysates were analyzed by SDS-PAGE and Western blotting as previously described in Yuan et al., (1996). Southern blotting and 2D gel electrophoresis was also performed to confirm loss of the acr gene and its gene product.

C. Results

We isolated the intact $\alpha$-crystallin chromosomal locus by screening a cosmid library of *M. tuberculosis* H37Rv with a probe corresponding to the α-crystallin open reading frame generated by PCR (GenBank Accession Number S79751). Southern blot-guided subcloning localized the gene to a 4 kb BamHI fragment. The 4 kb BamHI fragment containing the α-crystallin gene was restriction mapped and the entire α-crystallin gene was found to lie on an approximately 1 kb EcoRV fragment internal to the whole. In order to selectively excise this fragment we first removed, by restriction and religation, the EcoRV site in pBluescript and subcloned the 4 kb BamHI fragment into the corresponding site in the modified pBluescript. Digestion of this construct with EcoRV and subsequent insertion of a 1 kb hygromycin resistance cassette into the vector created the appropriate gene replacement construct containing approximately 1 kb of upstream sequence and 2 kb of downstream sequence with homology to the α-crystallin genomic locus in H37Rv.

Following linearization, this construct was used to transform H37Rv. Hygromycin resistant colonies were selected and grown to saturation and lysates were prepared individually from each. These lysates were analyzed by Western blotting using a monoclonal antibody to the α-crystallin protein (F22-2 provided by the WHO/CDC antibody collection). Screening of approximately 100 such colonies revealed the presence of one clone which failed to produce the α-crystallin protein but which appeared otherwise normal in its SDS-PAGE profile. Subsequent analysis of this clone by chromosomal Southern blots with the α-crystallin probe revealed that this gene was deleted and replaced with the hygromycin cassette. Thus this gene deletion appears to have resulted from a double homologous recombination event in which the α-crystallin gene locus was stably replaced with a hygromycin resistance cassette.

The resulting knockout strain was analyzed further by 2D gel electrophoresis to confirm the absence of the α-crystallin protein and to look for significant protein changes compared to wild type H37Rv. No significant changes in patterns of protein expression were noted, other than the absence of the α-crystallin protein.

Example 2
In vitro and in vivo Testing of Growth and Pathogenicity of the Knockout Strain This example shows that an α-crystallin protein knockout strain is indeed less pathogenic than the wild type strain from which it was generated and can replicate in vivo for a short period before being c.

A. In vitro Testing

The α-crystallin knockout strain of H37Rv has been evaluated for growth at 37° C. in aerated culture and does not display any significant difference in growth rate compared to wild type. In standing tube culture under oxygen-limitation, the growth rate of the knockout organism is somewhat impaired compared to wild type.

Growth of the knockout organisms was examined within the human macrophage cell line THP-1. Infectivity was unaffected, but growth of H37RvΔacr::hpt was substantially reduced compared to wild-type over the course of a 10-day infection. Growth of the knockout organism in primary mouse bone marrow-derived macrophages was also notably reduced over the course of a 6-day infection. Wild-type and knockout organisms were present in equivalent numbers 2 hours post-infection, indicating that the mutant was not impaired for macrophage attachment or entry, only growth.

B. In vivo Testing

C57BL/6 mice were infected intranasally with $1\times10^5$ CFU of either wild type H37Rv or the α-crystallin knockout strain. Analysis of colony forming units ("CFUs") recovered from the lungs of these mice five days after infection revealed that the mice infected with the knockout strain had a significant 0.5 log reduction in recoverable CFUs compared to mice infected with H37Rv. By three weeks after infection, mice infected with wild type H37Rv showed a much higher mortality rate than did those infected with the knockout strain. Analysis of tissue samples showed that animals infected with the wild type strain consistently had greater dissemination of mycobacteria throughout their organs, as well as greater numbers of mycobacteria present, than did animals infected with the knockout strain.

Example 3
The Role of the α-crystallin Heat Shock Protein in the Pathogenesis of *M. tuberculosis*

These studies were initiated to elucidate the environmental signals and mechanisms to which Acr expression responds and to understand the role of the Acr protein in the pathogenesis of tuberculosis.

A. Experimental Procedures

Growth of *M. tuberculosis* Under Different Oxygen Tensions

*M. tuberculosis* strain CSU93 was obtained from Dr. John Belisle, Colorado State University, Ft. Collins, Colo., under the Tuberculosis Research Materials Contract, NIAID. This organism, and strain H37Rv (ATCC 27294), were maintained in Middlebrook media as previously described (Yuan et al., (1996)). For growth under a defined oxygen atmosphere liquid cultures were propagated in insect cell culture flasks (Kontes Scientific Glassware/Instruments, Vineland, N.J.) customized by equipping the side arms with hose fittings and 0.2 μm filters; these were connected to a constant flow of premixed oxygen in nitrogen gas and vented into a Class II cabinet (Norco Gas, Missoula, Mont.). Gas flow was measured and adjusted to approximately 20 air changes per hour within each flask. Growth was monitored by removal of aliquots at the indicated time points and measuring the OD650 nm.

Acr Gene Replacement in *M. tuberculosis*

The gene replacement vector was constructed as described in Example 1, above, except that the construct was linearized with Ssp I. Two μg of this DNA was used to transform H37Rv, which was then plated on 7H11-OADC-hygromycin (50 μg/ml). Hygromycin-resistant single colonies were picked and grown to saturation in the presence of hygromycin. The bacteria were harvested by centrifugation, washed with PBS-Tween-80 (0.05%), and lysed in a Bead-Beater 8 (BioSpec Products, Bartlesville, Okla.) for 3 min. Lysates were analyzed by SDS-PAGE and Western blotting as previously described (Yuan et al., (1996)). Genomic DNA from the acr-knockout strain was digested with Pst I and ligated into pBluescript KS+ which was then used to transform *E. coli* to hygromycin resistance. A plasmid carrying the predicted 6 kb Pst I fragment was isolated and sequenced in entirety.

Reporter Vector Construction

The luciferase-reporter vector (pMH108) was made by PCR-amplifying the 254 nt region upstream of the ATG of the acr gene and cloning this between the phage T1/T2 transcription terminator and a promoterless firefly luciferase (luc) gene in the integrating mycobacteriophage vector pMH88 (Mdluli et al., *J. Inf Dis.* 174:1085–1090 (1996)) (hereafter Mdluli, et al., (1996)). To construct the green fluorescent protein ("GFP," from *Aequorea victoria*) reporter vector, the 550 bp Hind III-Xba I fragment containing the putative acr promoter and terminator was removed from pMH108 and ligated into the integrating vector pMV306. The 750 bp Hind III fragment containing the ORF of GFP was excised from pFPV27 (Valdivia et al., *Gene* 173:47–52 (1996)) and inserted into this construct.

Macrophage Infections

Mouse bone marrow-derived macrophages (BMDM) were prepared as previously described (Su et al., *Infect. Immun.* 63:946–953 (1995)). Briefly, cells eluted from mouse femurs were incubated in D-MEM-20, containing 20% FCS, $5\times10^{-5}$ M 2-ME (GibcoBRL, Life Technologies, Grand Island, N.Y.), 20% L-cell conditioned growth media and 10 μg/ml gentamicin for four days. After removal of nonadherent cells with Dulbecco's PBS with $Mg^{++}$ and $Ca^{++}$, BMDM were washed off and concentrated by centrifugation at 200×g for 5 min. The pelleted cells were resuspended and incubated in 24-well tissue culture plates at $6\times10^5$ cells per well in D-MEM-10 (10% FCS, 2ME, gentamicin and 200 U/ml of interferon-gamma) for two days. Human macrophage-like THP-1 cells (ATCC 202-TIB) at a concentration of $8\times10^5$ cells per well in 24-well plates were incubated in RPMI media with PMA (50 ng/ml) for 48 hr prior to infection. *M. tuberculosis* strains were grown in 7H9-ADC with appropriate antibiotics (kanamycin, 25 μg/ml or hygromycin, 50 μg/ml) to an OD650 nm of 0.5. Aliquots of this culture were stored at −80° C. and then titered from the frozen vial by plating serial dilutions in triplicate. Organisms were diluted in RPMI or D-MEM-10 and added to the macrophage monolayer in 24-well plates at an MOI of 1. After one hour incubation at 37° C., the inocula were removed from the wells, which were then washed five times with media. The macrophage cells were fed with fresh media and incubated in 5% C02 at 37° C. Cells in three identical wells were lysed at each timepoint with 0.4 ml of 1% Triton X-1 00, diluted in 7H9/ADC and plated in triplicate on 7H11-agar plates. CFUs were determined after incubation at 37° C. for three weeks. The GFP reporter experiments were done on glass coverslips containing a monolayer of THP-1 cells. After infection with the appropriate strain as above and incubation for the specified time period, cells were fixed with 2.5% glutaraldehyde-PBS at 4° C. for 24 hours. Fluorescent bacteria were photographed on a Nikon FXA photomicroscope using a 60× planapochromat objective. Luciferase activity was monitored as previously described (Mdluli, et al. (1996)).,

Other Procedures

Two-dimensional gel electrophoresis was performed as previously described (Yuan et al., (1996)). Genomic DNA was prepared from *M. tuberculosis* using Bose's protocol (Bose et al., *Nucl Acids Res.* 21:2529–2530 (1993)). Southern blotting was done with QuickHyb hybridization solutions, and the blots were washed under stringent conditions as described by the manufacturer (Stratagene, La Jolla, Calif.). *M. tuberculosis* was transformed by electroporation with various constructs at 37° C. (Yuan et al., *J. Bio. Chem.* 272:10041–10049 (1997)). Restriction endonucleases, DNA-modifying enzymes, and T4 DNA ligase were purchased from New England Biolabs (Beverly, Mass.). Plasmids or DNA fragments were purified and isolated with QIAGEN plasmid kit, QIAquick Nucleotide Removal Kit or Gel Extraction Kit (QIAGEN Inc., Chatsworth, Calif.).

B. Results

Acr Expression is Regulated by a Transcriptional Repressor in Response to Atmospheric Oxygen Concentration Initial experiments to determine the nature of the environmental signal to which Acr production was responsive demonstrated that transferring a culture from rolling to standing was sufficient to induce expression (Yuan et al., (1996)). We then grew a recent clinical isolate of *M. tuberculosis* (CSU93) under a constant flow of an atmosphere of defined oxygen concentration. In early logarithmically growing rolling culture under normal atmospheric oxygen pressure (20%) no Acr was visible by two-dimensional gel electrophoresis but upon reduction of the oxygen concentration to 1.3% the protein was abundantly produced.

To investigate this regulation in more detail, transcriptional fusions of the upstream 250 nt of the acr gene were constructed with a promoterless β-galactosidase gene in an integrating vector based upon mycobacteriophage L5 (Mdluli et al., (1996); Stover et al., *J. Exp. Med.* 178:197–209 (1993)). Sealed early log-phase cultures of *Mycobacterium tuberculosis* var. *bovis* BCG that had been transformed with this reporter were repeatedly purged with gas containing a defined concentration of oxygen in nitrogen and these were grown for an additional 6 hours before assaying β-galactosidase activity. In this time frame, significant levels of promoter activity were observed at oxygen concentrations below 5.3%, and this activity continued to increase as oxygen concentration was lowered to 0.7% oxygen. To identify the mechanism of this transcriptional regulation, we PCR-amplified DNA segments corresponding to sequential 30–50 nt deletions of the acr promoter region and cloned these separately into a reporter vector in which expression from the acr promoter is monitored by luciferase expression from the fflux gene (Mdluli et al., (1996)). Following integration, each deletion was assayed for promoter activity in aerated and standing tube culture. These studies demonstrated that the 167 nucleotides (nt) upstream of the acr gene start codon were sufficient to maintain oxygen inducibility. Further deletion of 35 nt resulted in constitutive promoter activation independent of oxygen concentration, suggesting that the deleted nucleotides form a binding site for a repressor that inhibits acr transcription in the presence of high oxygen levels. Still further deletion of nt −87 to −42 resulted in loss of the constitutive promoter activity, suggesting that this region may contain the basal promoter element.

Acr is Expressed During the Course of Macrophage Infections in vitro

The induction of Acr expression in mildly hypoxic conditions suggested that the protein might be expressed in the course of active infections. The 254 nucleotide sequence containing the acr promoter and putative repressor binding site was fused to a promoterless green fluorescent protein gene derived from the gfp gene of *Aequorea victoria* on the integrative mycobacterial vector pMV306. This construct was transformed into H37Rv and expression was monitored by fluorescence microscopy. As expected, log-phase organisms grown aerobically in vitro were non-fluorescent while organisms grown under low-oxygen conditions were brightly fluorescent. When these organisms were used to infect human macrophage-like THP-1 cells and observed under a fluorescence microscope, fluorescent bacteria were easily observed within these cells 12–48 hours later. With the promoter in the opposite orientation, no fluorescence was observed. To assess quantitatively the macrophage-dependent induction of acr gene expression, the H37Rv strain carrying the acr promoter-lux fusion was incubated with THP-1 cells and assays of luciferase activity were performed. Induction of the acr promoter was evident within one hour, while entry into macrophage was still underway. Within four hours, acr-promoter driven luciferase expression was induced more than one-hundred fold. In contrast, bacilli suspended in cell culture media did not induce acr expression even at 24 hours.

Construction of an Acr Null Mutant of *M. tuberculosis*

An Acr knockout strain was created by replacing the 1 kb acr gene embedded within a 4 kb genomic fragment with a hygromycin resistance cassette to give a construct with acr homologous upstream and downstream sequence surrounding the resistance marker. This construct, on a plasmid incapable of replicating in *M. tuberculosis*, was linearized and cultures from hygromycin-resistant colonies (10–20 per µg of DNA) were analyzed by SDS-PAGE and Western Blotting using a monoclonal antibody specific to the Acr protein (Yuan et al., (1996)). Out of 100 such colonies, one was shown to lack immunoreactivity and was characterized further. Chromosomal DNA from this strain was analyzed by Southern blotting and found to have acquired the sequence corresponding to the hygromycin resistance cassette used for gene replacement while lacking the acr gene sequence. In addition, this strain still possessed the cma1 gene, a marker that uniquely identifies the pathogenic mycobacteria (Yuan et al., *Proc. Natl. Acad. Sci. USA* 92:6630–6634 (1995)). The 2-dimensional gel electrophoretic profile of stationary-phase organisms of this strain confirmed the lack of the Acr protein. Reisolation of the chromosomal fragment carrying the hygromycin resistance cassette and sequence analysis of the junction regions outside the homologous regions carried by the initial knockout construct confirmed the resistance gene was inserted by homologous recombination into the acr locus. Interestingly no compensatory changes in protein expression were observed in the knockout compared with the wild type strain.

Acr Null Mutants Are Impaired for Growth within Macrophages and for Long-term Survival in vitro We examined growth of the Acr deletion strain H37RvΔacr::aph in vitro, but no significant differences were observed even under low oxygen conditions. There was also no significant difference in sensitivity to in vitro killing by hydrogen peroxide between H37Rv and H37RvΔacr::aph. We then examined growth of organisms within the human macrophage-like cell line THP-1. Infectivity was unaffected but growth of H37RvΔacr::aph was substantially reduced compared to wild-type over the course of a 10 day infection. An analysis of the growth of the knockout organism in primary mouse bone marrow-derived macrophages also revealed a notable reduction in replication over the course of a 6 day infection. Equivalent numbers of knock out mutant and H37Rv organisms were present 2 hours post-infection, indicating that the mutant was not impaired for macrophage attachment or entry, only survival. Log-phase organisms were used in both of these infections, so that initially neither strain was expressing Acr. Infections with wild type organisms grown to stationary phase with high-levels of Acr were identical in longterm macrophage infections. These infections did not reveal a significant difference in survival during early infection regardless of Acr status.

We also assessed the long-term survival of the Acr knockout in static non-growing cultures and found that over the course of three months in hypoxic conditions without growth a fourfold-difference in survival was seen. Under such conditions, 23% of the initial inoculum of H37Rv remains viable upon plating but only 5.6% of the initial inoculum of the knockout strain retains such viability.

C. Discussion

The ability of *M. tuberculosis* strains to grow under reduced oxygen tension in vitro is directly correlated with the ability of such strains to cause disease (Heplar et al., *J. Inf Dis.* 94:90–98 (1953); Guy et al., *J. Inf Dis.* 94:99–106 (1953)). In addition to our earlier work associating Acr with *M. tuberculosis* dormancy, we have now shown that expression of acr is rapidly and powerfully induced in vivo upon entry into macrophages or in vitro upon oxygen deprivation. These data invite reevaluation of both of the nature of the intracellular milieu experienced by *M. tuberculosis* and the physiological role of the Acr protein during infection. Human alveolar macrophage are presumably exposed to higher oxygen concentrations than other leukocytes (Fels et al., *J. Applied Physiol.* 60: 353–369 (1986)), but the actual oxygen tension within these cells is unknown. While additional means of regulation cannot be excluded, the robust (>100-fold) induction of acr-luciferase fusions on infection of cultured macrophages, similar in magnitude to the maximum achievable under hypoxic conditions in vitro, suggests that the oxygen concentration within these macrophages is low. Thus, contrary to the long-standing idea that low-oxygen conditions are unique to the caseous granuloma, growth under oxygen limitation may be the norm for tubercle bacilli and in vitro propagation techniques at atmospheric oxygen may be atypical.

Due to its earlier association with *M. tuberculosis* latency in vitro, the role of Acr in intracellular growth within macrophages described here was unexpected. In other systems and in *M. tuberculosis*, Acr has been shown to function as a chaperonin, protecting other cellular proteins from degradation (Horwitz, J., *Proc. Natl. Acad. Sci. USA* 89:10449–10453 (1992); Groenen et al., *Eur. J. Biochem.* 225:1–19 (1994)). However, the hypoxic conditions that induce Acr expression seem unlikely to result in protein instability. Oxygen limitation may instead serve as a signal of the hostile intracellular environment, with Acr expression necessary to protect against other stresses inherent to that environment. In this regard, it is curious that the knockout strain is not more sensitive to low pH, nutrient deprivation and hydrogen peroxide and that such stresses fail to induce Acr expression (Yuan et al., (1996)). The nature of the intracellular bacteriocidal effector against which Acr protects *M. tuberculosis* during growth in macrophages remains unknown.

Production of Acr exacts a toll in terms of growth rate of expressing organisms in vitro therefore production is most likely essential to survival under some conditions. The repression of expression in atmospheric oxygen levels suggests the possibility that this regulatory mechanism has been maintained to promote rapid growth in a highly oxygenated environment. Such an environment might occur uniquely in the context of the in situ alveolar macrophage or it may occur later in the infectious cycle of tuberculosis when caseous granulomas undergo liquefaction and the lung wall disintegrates (Dannenberg, A. M., Jr., *Hosp. Pract.* 15:51–58 (1993)). In this scenario, down-regulation of Acr protein expression may contribute to transmission of disease by facilitating rapid extracellular growth of the organism to high titer prior to discharge in aerosolized sputum. The availability of the Acr knockout strain will allow for testing of such hypotheses in animal models of both persistence and acute infection as well as providing a vehicle for the production of a new live vaccine for tuberculosis.

SEQUENCES

The amino acid sequence of α-crystallin heat shock protein (SEQ ID NO:2) is as follows: Total amino acids are 144.

1 mattlpvqrh prslfpefse lfaafpsfag lrptfdtrlm rledemkegr
51 yevraelpgv dpdkdvdimv rdgqltikae rteqkdfdgr sefaygsfvr
101 tvslpvgade ddikatydkg iltvsvavse gkptekhiqi rstn The nucleic acid sequence of the acr gene (SEQ ID NO:1) is as follows:

BASE COUNT 94 A 148 C 142 G 90 T
ORIGIN
1 ATTAGGAGGC ATCAAATGGC CACCACCCTT CCCGTTCAGC GCCACCCGCG GTCCCTCTTC
61 CCCGAGTTTT CTGAGCTGTT CGCGGCCTTC CCGTCATTCG CCGGACTCCG GCCCACCTTC
121 GACACCCGGT TGATGCGGCT GGAAGACGAG ATGAAAGAGG GGCGCTACGA GGTACGCGCG
181 GAGCTTCCCG GGTCGACCC CGACAAGGAC GTCGACATTA TGGTCCGCGA TGGTCAGCTG
241 ACCATCAAGG CCGAGCGCAC CGAGCAGAAG GACTTCGACG GTCGCTCGGA ATTCGCGTAC
301 GGTTCCTTCG TTCGCACGGT GTCGCTGCCG GTAGGTGCTG ACGAGGACGA CATTAAGGCC
361 ACCTACGACA AGGGCATTCT TACTGTGTCG GTGGCGGTTT CGGAAGGGAA GCCAACCGAA
421 AAGCACATTC AGATCCGGTC CACCAACTGA CCACTGGGTC CGTGCTGATG ACCG

---

SEQUENCE LISTING

<160> NUMBER OF SEQ ID NOS: 2

<210> SEQ ID NO 1
<211> LENGTH: 474
<212> TYPE: DNA
<213> ORGANISM: Mycobacterium tuberculosis
<220> FEATURE:
<221> NAME/KEY: CDS
<222> LOCATION: (16)..(450)
<223> OTHER INFORMATION: alpha-crystallin heat sho ck protein acr gene

<400> SEQUENCE: 1

```
attaggaggc atcaa atg gcc acc acc ctt ccc gtt cag cgc cac ccg cgg          51
              Met Ala Thr Thr Leu Pro Val Gln Arg His Pro Arg
                1               5                  10 tcc ctc ttc ccc gag ttt tct gag ctg ttc g cg gcc ttc ccg tca ttc          99
Ser Leu Phe Pro Glu Phe Ser Glu Leu Phe A la Ala Phe Pro Ser Phe
         15                  20                 25 gcc gga ctc cgg ccc acc ttc gac acc cgg t tg atg cgg ctg gaa gac         147
Ala Gly Leu Arg Pro Thr Phe Asp Thr Arg L eu Met Arg Leu Glu Asp
     30                  35                  40 gag atg aaa gag ggg cgc tac gag gta cgc g cg gag ctt ccc ggg gtc         195
Glu Met Lys Glu Gly Arg Tyr Glu Val Arg A la Glu Leu Pro Gly Val
 45                  50                  55                  60 gac ccc gac aag gac gtc gac att atg gtc c gc gat ggt cag ctg acc         243
Asp Pro Asp Lys Asp Val Asp Ile Met Val A rg Asp Gly Gln Leu Thr
                 65                  70                  75 atc aag gcc gag cgc acc gag cag aag gac t tc gac ggt cgc tcg gaa         291
Ile Lys Ala Glu Arg Thr Glu Gln Lys Asp P he Asp Gly Arg Ser Glu
             80                  85                  90 ttc gcg tac ggt tcc ttc gtt cgc acg gtg t cg ctg ccg gta ggt gct         339
Phe Ala Tyr Gly Ser Phe Val Arg Thr Val S er Leu Pro Val Gly Ala
         95                 100                 105 gac gag gac gac att aag gcc acc tac gac a ag ggc att ctt act gtg         387
Asp Glu Asp Asp Ile Lys Ala Thr Tyr Asp L ys Gly Ile Leu Thr Val
     110                 115                 120 tcg gtg gcg gtt tcg gaa ggg aag cca acc g aa aag cac att cag atc         435
Ser Val Ala Val Ser Glu Gly Lys Pro Thr G lu Lys His Ile Gln Ile
125                 130                 135                 140 cgg tcc acc aac tga ccactgggtc cgtgctgatg accg                            474
Arg Ser Thr Asn
            145
```

<210> SEQ ID NO 2
<211> LENGTH: 144
<212> TYPE: PRT
<213> ORGANISM: Mycobacterium tuberculosis
<220> FEATURE:
<223> OTHER INFORMATION: alpha-crystallin heat sho ck protein

<400> SEQUENCE: 2

```
Met Ala Thr Thr Leu Pro Val Gln Arg His P ro Arg Ser Leu Phe Pro
 1               5                  10                 15

Glu Phe Ser Glu Leu Phe Ala Ala Phe Pro S er Phe Ala Gly Leu Arg
            20              25                  30

Pro Thr Phe Asp Thr Arg Leu Met Arg Leu G lu Asp Glu Met Lys Glu
            35              40                 45

Gly Arg Tyr Glu Val Arg Ala Glu Leu Pro G ly Val Asp Pro Asp Lys
        50              55                 60

Asp Val Asp Ile Met Val Arg Asp Gly Gln L eu Thr Ile Lys Ala Glu
 65             70                  75                  80

Arg Thr Glu Gln Lys Asp Phe Asp Gly Arg S er Glu Phe Ala Tyr Gly
            85              90                  95

Ser Phe Val Arg Thr Val Ser Leu Pro Val G ly Ala Asp Glu Asp Asp
            100             105                 110

Ile Lys Ala Thr Tyr Asp Lys Gly Ile Leu T hr Val Ser Val Ala Val
            115             120                 125

Ser Glu Gly Lys Pro Thr Glu Lys His Ile G ln Ile Arg Ser Thr Asn
        130             135                 140
```

What is claimed is:

1. A strain of Mycobacterium sp. wherein the expression level of α-crystalline heat shock protein ("acr protein") gene is reduced by at least 75% compared to the wild type expression level of acr protein of living members of the same species.

2. A strain of claim 1 wherein the Mycobacterium sp. is selected from the group consisting of *M. tuberculosis* and *M. bovis*.

3. A strain of claim 1 wherein the expression level of α-crystallin heat shock protein gene is eliminated.

4. A strain of claim 1 wherein the expression level of α-crystallin heat shock protein gene is eliminated by means of deletion of the gene.

5. A strain of claim 1 wherein the strain is housed in a sealed vial where the vial is packaged with instructional material stating a method of injecting the strain into a human to provide the human with immunoprotection from tuberculosis.

6. A method of manufacturing attenuated mycobacteria wherein the method comprises reducing expression of the α-crystallin heat shock protein by at least 75% of the wild type expression level.

7. The method of claim 6, wherein the method of reducing expression of the α-crystallin heat shock protein is by deletion of the gene encoding the protein.

8. The method of claim 6, wherein the mycobacteria attenuated is selected from the group consisting of *M. tuberculosis* and *M. bovis*.

9. A method for attenuating virulence of a Mycobacterium sp., said method comprising reducing the expression level of α-crystallin heat shock protein gene by at least 75% of the wild type expression level of said Mycobacterium sp.

10. The method of claim 9, wherein the method of attenuating virulence is by deletion of the gene encoding the α-crystallin heat shock protein.

11. The method of claim 9, wherein the Mycobacterium sp. whose virulence is attenuated is selected from the group consisting of *M. tuberculosis* and *M. bovis*.

\* \* \* \* \*